US011724084B2

(12) United States Patent
Hougaard et al.

(10) Patent No.: US 11,724,084 B2
(45) Date of Patent: *Aug. 15, 2023

(54) FLEXIBLE DOUBLE LUMEN TUBE AND A TUBE COUPLING SYSTEM FOR SAME

(71) Applicant: MBH-INTERNATIONAL A/S, Allerød (DK)

(72) Inventors: Ole Hougaard, Helsingør (DK); Henrik Bork Bjerregaard, Lynge (DK)

(73) Assignee: MBH-INTERNATIONAL A/S, Allerod (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/513,114

(22) Filed: Oct. 28, 2021

(65) Prior Publication Data

US 2022/0047860 A1 Feb. 17, 2022

Related U.S. Application Data

(63) Continuation of application No. 16/979,806, filed as application No. PCT/DK2019/050079 on Mar. 6, 2019, now Pat. No. 11,160,968.

(30) Foreign Application Priority Data

Mar. 12, 2018 (DK) .......................... PA 2018 70156

(51) Int. Cl.
*A61M 39/10* (2006.01)
*A61M 3/02* (2006.01)
(Continued)

(52) U.S. Cl.
CPC ........ *A61M 39/105* (2013.01); *A61M 3/0295* (2013.01); *F16L 37/0841* (2013.01);
(Continued)

(58) Field of Classification Search
CPC ..... F16L 37/0841; F16L 37/00; F16L 37/084; F16L 37/086; F16L 39/00; F16L 39/02;
(Continued)

(56) References Cited

U.S. PATENT DOCUMENTS 3,856,051 A 12/1974 Bain
3,986,732 A 10/1976 Stanley
(Continued)

FOREIGN PATENT DOCUMENTS

DE 8513803 U1 6/1985
DE 102016007578 A1 12/2017
(Continued)

OTHER PUBLICATIONS

International Search Report and Written Opinion, Appl. No. PCT/DK2019/050079 dated Jul. 1, 2019.
(Continued)

*Primary Examiner* — Zachary T Dragicevich
*Assistant Examiner* — William S. Choi
(74) *Attorney, Agent, or Firm* — Fox Rothschild LLP

(57) ABSTRACT

A tube coupling component (4;6) serves for use in a tube coupling system and an irrigation system. The tube coupling component (4;6) comprises a male coupling part (12) opposite a respective female coupling part (11), or a first end fitting (33) opposite a respective second end fitting (34), which tube coupling component (4;6) has an interior pipe (13;31) that extends axially inside an exterior pipe (14;32), wherein the interior pipe (13;31) and the exterior pipe (14;32) are concentric.

10 Claims, 8 Drawing Sheets

(51) Int. Cl.
*A61M 25/10* (2013.01)
*F16L 37/084* (2006.01)
*F16L 37/56* (2006.01)

(52) U.S. Cl.
CPC ............ *F16L 37/565* (2013.01); *A61M 25/10* (2013.01); *A61M 25/1006* (2013.01); *A61M 2210/1067* (2013.01)

(58) Field of Classification Search
CPC ........ F16L 11/20; F16L 11/22; F16L 25/1025; F16L 25/1034; F16L 37/56; F16L 37/565; F16L 37/144; A61M 39/105; A61M 3/0295; A61M 2210/1067; A61M 39/10; A61M 2039/1077; A61M 25/10; A61M 25/1006; A61M 2025/1061
USPC ........ 285/1, 305, 307, 308, 317, 319, 124.1, 285/310
See application file for complete search history.

(56) References Cited

U.S. PATENT DOCUMENTS

| | | | |
|---|---|---|---|
| 4,403,612 A | | 9/1983 | Fogarty |
| 5,401,064 A | * | 3/1995 | Guest .................... F16L 37/565 |
| 5,628,532 A | * | 5/1997 | Ashcraft ................. F16L 11/22 |
| 5,782,502 A | * | 7/1998 | Lewis .................... F16L 37/144 |
| | | | 285/305 |
| 5,863,077 A | * | 1/1999 | Szabo .................... F16L 37/144 |
| 5,951,063 A | * | 9/1999 | Szabo .................... F16L 37/144 |
| | | | 285/319 |
| 5,981,063 A | | 11/1999 | Yokozeki et al. |
| 6,446,661 B2 | | 9/2002 | Armenia et al. |
| 6,550,815 B2 | * | 4/2003 | Zitkowic, Jr. ......... F16L 37/144 |
| | | | 285/319 |

| | | | |
|---|---|---|---|
| 2004/0099268 A1 | | 5/2004 | Smith et al. |
| 2004/0244848 A1 | | 12/2004 | Maldavs |
| 2005/0065544 A1 | | 3/2005 | Yamaguchi et al. |
| 2007/0106213 A1 | | 5/2007 | Spera et al. |
| 2007/0241560 A1 | * | 10/2007 | Malone ................. F16L 37/565 |
| | | | 285/319 |
| 2007/0289645 A1 | | 12/2007 | Schutz |
| 2010/0052315 A1 | | 3/2010 | Kerin et al. |
| 2012/0143168 A1 | | 6/2012 | Bjerregaard |
| 2012/0215166 A1 | | 8/2012 | Barki |
| 2013/0049355 A1 | | 2/2013 | Weinhold |
| 2014/0339821 A1 | | 11/2014 | Ishizaka et al. |
| 2016/0252201 A1 | | 9/2016 | Chintalapati et al. |
| 2017/0350548 A1 | | 12/2017 | Tiberghien et al. |
| 2017/0361084 A1 | | 12/2017 | Zergiebel et al. |

FOREIGN PATENT DOCUMENTS

| | | |
|---|---|---|
| EP | 0082950 A2 | 7/1983 |
| EP | 0669142 A2 | 8/1995 |
| EP | 2967608 A2 | 1/2016 |
| GB | 1253959 A | 11/1971 |
| KR | 935300 B1 * | 1/2010 |
| WO | 2011023196 A1 | 3/2011 |
| WO | 2014169057 A1 | 10/2014 |

OTHER PUBLICATIONS

International Preliminary Examining Report (IPEA) and Written Opinion, Appl. No. PCT/DK2019/050079 dated Nov. 26, 2019.
International Preliminary Report on Patentability (IPRP), Appl. No. PCT/DK2019/050079 dated Jun. 25, 2020.
Examination Report dated Jan. 13, 2020 in related Danish Patent Application No. PA 2019 70637; 9 pgs.
Examination Report dated Jun. 21, 2021 is relaated Danish Patent Application No. PA 2021 70138; 10 pgs.

* cited by examiner

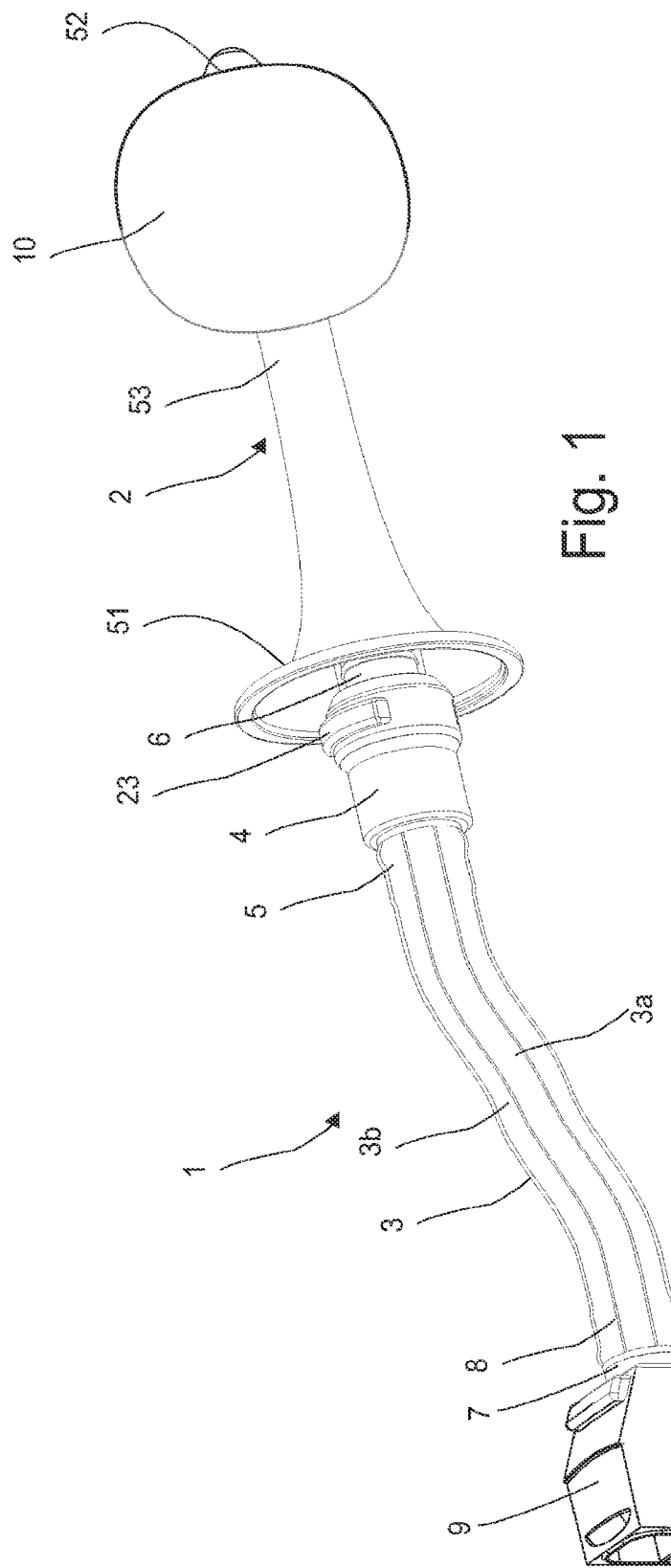
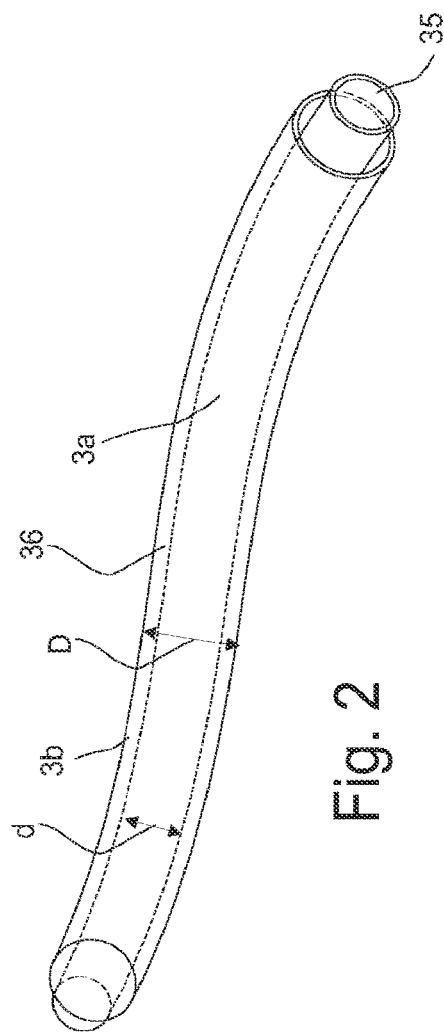

FLEXIBLE DOUBLE LUMEN TUBE AND A TUBE COUPLING SYSTEM FOR SAME

CROSS-REFERENCE TO RELATED APPLICATIONS

This application is a continuation of U.S. patent application Ser. No. 16/979,806, filed Sep. 10, 2020, issuing Nov. 2, 2021 as U.S. Pat. No. 11,160,968, which is a 371 of International Patent Application PCT/DK2019/050079, filed Mar. 6, 2019, which claims the benefit of priority to DK Patent Application No. PA 2018 70156, filed Mar. 12, 2018, the disclosure of each is incorporated herein by reference in its entirety.

TECHNICAL FIELD

The present invention further relates to a tube coupling system for a flexible double lumen tube, in particular a medical flexible double lumen tube that can provide fluid communication between one or two sources of liquid pr gas and a double lumen irrigation device having annular arranged connection pieces for axially extending lumens.

BACKGROUND OF THE INVENTION

Double lumen tubes are known from endotracheal ventilation applications. These known double lumen tubes have a large diameter ventilation tube and a much smaller diameter inflating tube for inflating a cuff. The inflating tube is provided exterior to the ventilation tube and each tube have each their individual coupling piece at free separate lengths of each tube for connecting to a source of air.

The applicant's international patent application no. PCT/DK2017/050338 discloses a transanal irrigation catheter having a first channel to supply a fluid to a balloon in order to expand the balloon and fix the catheter in a position in the rectum. This transanal rectal catheter has a second channel inside which the first channel extends, which second channel is coupled to a reservoir of irrigation liquid to be supplied to the patient, and which first channel is coupled to a reservoir of expansion fluid to be supplied to an expandable cuff. The first channel and the second channel have similar annular arranged connection pieces but need a special converter to allow the irrigation catheter to be coupled to tubes that communicate with the respective reservoir(s). The converter of this known system converts annular flow through annular arranged connection pieces into parallel flow through parallel connection pieces for parallel arranged tubes to the respective reservoirs, optionally to same reservoir via a valve device.

This arrangement is very effective but some patients experience problems mating tubes and connection pieces.

SUMMARY OF THE INVENTION

The present invention provides improvements to the above known irrigation system by in a first aspect providing a tube connector adapted for coupling annularly arranged tubes to annularly arranged tube connection pieces, in a second aspect providing an annular flow system of two annularly arranged tubes, in a third aspect providing a tube coupling system which provides fluid communication from annularly arranged connection pieces of a device having annularly arranged flow channels to fluid reservoirs, and in a fourth aspect providing a tube coupling system for a double lumen tube that ensures sustained fluid flow.

The novel and unique whereby these and other aspects are achieved according to the present invention consists in a tube coupling component comprising a male coupling part opposite a respective female coupling part, or a first end fitting opposite a respective second end fitting, which tube coupling component has an interior pipe that extends axially inside an exterior pipe, wherein the interior pipe and the exterior pipe are concentric.

A flexible double lumen tube is a flexible annular double lumen tube having an interior flexible tube extending inside an exterior flexible tube, wherein the interior flexible tube delimits a first flow channel, and the annular tube gap between said interior flexible tube and said exterior flexible tube delimits a second flow channel.

There is a prejudice within the art to use an annular double lumen tube because the interior flexible tube arranged inside the exterior flexible tube can move freely radially so that sustained fluid flow through the annular tube gap may vary. The advantage is however the reduction in combined exterior volume and a well-defined exterior surface due to said exterior surface being the exterior surface of the exterior flexible tube. The exterior surface of the interior flexible tube is not exposed to the environment and thus protected inside the exterior flexible tube.

The interior flexible tube has an exterior diameter that is smaller than an interior diameter of the exterior flexible tube to delimit the annular tub gap, and the interior flexible tube has no connections to the exterior flexible tube. Accordingly, the flexible annular double lumen tube according to the present invention has no radial struts or radial spacers that lengthwise of the flexible annular double lumen tube serves to keep the annular tube gap open. A plurality of such struts or spacers along the length of the flexible annular double lumen tube would make the flexible annular double lumen tube rigid and less bendable, and moreover struts or spaces are obstacles in the flow channel that would reduce flow speed along the entire flow length. The flexible interior tube can move radially inside the flexible exterior whereby the cross-sectional flow area at a given cross-section remains substantially the same irrespective of the radial location of the interior flexible tube in relation to the exterior flexible tube. The flexible interior tube is thus loosely arranged inside the exterior flexible tube, which provides the further advantage that the combined annular double lumen tube is little vulnerable to kinking in response to bending.

The present invention further provides a novel and unique tube coupling system having one or more end fittings to be plugged to the free ends of the flexible annular double lumen tube.

The flexible annular double lumen tube is particular easy to provide with/connect to a tube coupling system if the loosely arranged interior flexible tube inside the exterior flexible tube is longer than the exterior flexible tube, e.g. between 3-10 mm longer. At least one end of the interior flexible tube can thus protrude from the exterior flexible tube, but preferably both ends of the interior flexible tube can protrude from the exterior flexible tube. The "extra" length of the interior flexible tube compared to the length of the exterior flexible tube is, in use with the tube coupling system, distributed along the entire length of the flexible annular double lumen tube. Since the extra length is short compared to the overall length of the flexible annular double lumen tube no bulking or kinking of the interior flexible tube inside the exterior flexible tube and the end fittings keeps the position of the interior flexible tube relative to the exterior flexible tube lengthwise, and at the end fittings also the radial relative position of said tubes. The extra length of interior flexible tube compared to the length of the exterior flexible tube may typically be less than 1%.

The end fitting system of the tube coupling system comprises
  a first coupling component that has a female coupling part that axially extends into an opposite male coupling part,
    the male coupling part is adapted for coupling to a proximal end of the flexible annular double lumen tube by being configured with
      a first interior pipe inside a first exterior pipe, said first interior pipe is adapted for sealingly coupling to the interior flexible tube of the flexible annular double lumen tube to establish fluid communication to the first flow channel, and
      said first exterior pipe is adapted for sealingly coupling to the exterior flexible tube of the flexible annular double lumen tube to establish fluid communication to the second flow channel, and
    a second coupling component has a second interior pipe that axially extends inside a second exterior pipe, wherein
      the second coupling component has a first end fitting adapted for coupling to at least the female coupling part of the first coupling component, and
      an opposite second end fitting adapted for coupling to any of the flexible annular double lumen tube or to similarly configured annularly arranged flexible connection pieces of an annular double lumen device to establish fluid communication to the first and the second flow channel via the interconnected first coupling component and the second coupling component.

The first coupling component and the second coupling component of the end fitting system is dimensioned and configured to fit for coupling with the flexible annular double lumen tube. To do that the male coupling part of the first coupling component has a first interior pipe that fits inside the interior flexible tube to establish fluid communication there-through. The exterior flexible tube is mounted around the first exterior pipe to provide fluid communication to the annular tube gap that constitutes the second flow channel. Due to the annular arrangement of the first interior pipe and the first exterior pipe the male coupling part of the first coupling component is easily plugged into a free end of the flexible annular double lumen tube.

The second coupling component has a multifunctional design providing a very versatile usability.

On the one hand the first end fitting of the second coupling part is adapted for at least coupling to the female coupling part of the first coupling component. The opposite second end fitting is then used to couple to a device configured with flexible annularly arranged connection pieces to establish two annularly arranged flow passages through the interconnected first coupling component and second coupling component between the device and the flexible annular double lumen tube. Such a device can be a medical device, including but not limited to a transanal irrigation catheter and irrigation via a stoma.

The second end fitting may, just as the first end fitting, also fit to couple to a free end of the flexible annular double lumen tube, and can be used e.g. at the distal end of said annular double lumen tube. Because both ends of the second coupling component is configured to couple to the flexible annular double lumen tube the second coupling component is also very useful to join lengths of the flexible annular double lumen tube, so that the user can make any length he/she desires based on pieces of standard lengths of annular double lumen tube. The second coupling component is a very useful tool in customizing the length of the flexible annular double lumen tube.

In order that the annular tube gap is kept optimum open at the inlet the first interior pipe and the second exterior pipe of the first coupling component may be arranged concentric. The concentric arrangement of the first interior pipe and the second exterior pipe also makes the orientation and angle change of the second coupling component about its longitudinal axis immaterial. It does not matter how the second coupling component is rotated about its longitudinal axis to mate any of the first coupling component, similarly concentrically arranged flexible connection pieces of a device, such as an irrigation catheter, or mate a free end of the flexible annular double lumen tube.

If the flexible connection pieces also are concentric the angular orientation of the device, to which the second coupling component is to be coupled, along the longitudinal axis of the device also becomes immaterial, and it is very easy for the user to couple the flexible annular double lumen tube to the device to operate the device because he/she needs not take orientation into account. However because the annular double lumen tube and the annular concentrically arranged flexible connection pieces have inherent flexibility a concentric arrangement would be possible and acceptable.

A significant advantage is that the second coupling piece can be mounted to the device prior to using the device. The first coupling piece can be coupled with the second coupling piece on the device, prior to use, or during use of the device, and the first coupling piece and the second coupling piece can easily be decoupled after use of the device. The flexible annular double lumen tube can be disposed or reused after rinsing with e.g. fresh tap water. The device coupled to the flexible annular double lumen tube can also be reused by rinsing with tap water, or be disposed.

Advantageously, if the second end fitting and the male coupling part have the same cross-section the second end fitting and the male coupling part have same functionality and can be used interchangeably.

The second interior pipe may protrude beyond the second exterior pipe at the first end fitting to be used to improve and facilitate guiding of the first end fitting in engagement with e.g. the flexible annular double lumen tube or the female coupling part. A protruding second interior pipe is especially easy to secure inside a interior flexible tube protruding from an exterior flexible tube. When the second interior pipe is longer than the second exterior pipe the sealing engagement between the flexible annular double lumen tube is improved.

As described the second interior pipe can protrude beyond the second exterior pipe which is beneficial when coupling the first end fitting of the second coupling in sealing engagement with the female coupling part of the first coupling component.

At the opposite second end fitting of the second coupling component the second interior pipe may be fully inside the second exterior pipe so that the respective free ends are flush and in substantially same plane, or the second exterior pipe may protrude slightly, such as between 0.1-2% of its length, beyond the second interior pipe, thereby providing the second coupling component with a coupling functionality alternative to the coupling functionality of the first end fitting which is particular convenient if coupling length, thus overlap between second coupling component and flexible double lumen tube are short, e.g. if the flexible annular connection pieces of the device in itself are short. The axial length of the second end fitting is preferably so long that the full length of the second end fitting can be coupled to flexible connection pieces of the device. Both the first end fitting and the second end fitting can couple to the flexible annular double lumen tube.

To further facilitate pushing the exterior flexible tube lengthwise onto the free end of the second exterior pipe at the first end fitting, the second exterior pipe may have an external tapering towards its free end.

At least one of the first end fitting, the second end fitting, and the male coupling part may have an annular barb to improve engagement with the flexible annular double lumen tube and/or the flexible annular connection pieces.

The female coupling part of the first coupling component is delimited by a circumferential wall having opposite first and second lock slots for slidingly, crosswise the longitudinal axis of the first coupling component, receiving a first ring-shaped lock component to, at least temporarily, lock the first end fitting of the second coupling component firmly together with the female coupling part of the first coupling component.

The first ring-shaped lock component may advantageously have a first end that, via opposite exterior straight slide surfaces, extends into an opposite second end. Preferably said first end and said second end are curved, preferably curved to follow substantially the exterior outline of the female coupling part. Preferably the first end curves away from the opposite second end. A hole of the first ring-shaped lock component may expediently serve for inserting the first end fitting, and the first end of the first ring-shaped lock component may serve as a push button arranged to be accessible via the first lock slot. The opposite second end of the first ring-shaped lock component may be configured with an annular spring member that extends a sector of the circumference of the lock ring opposite the curved first end. The annular extent of the annular spring member may be longer than the length of the second lock slot so that the first ring-shaped lock component cannot be pushed out of the second slot. The annular spring member advantageously clamps the first ring-shaped lock component in firm engagement around the first end fitting.

The female coupling part may have a seat for a gasket, which seat has its bottom at the transmission between the male coupling part and the female part component. The overall shape of the first coupling component is substantially a funnel-shape where the female coupling part is wider than the male coupling part, and in that the first exterior pipe has various diameters along its length. The female coupling part of the first coupling component has an internal diameter corresponding to at least the largest exterior diameter of the first end fitting of the second coupling component to receive said first end fitting, whereby the second coupling component has a smaller exterior diameter than the exterior diameter of the first coupling component.

The gasket serves to seal the transition between the female coupling part and the male coupling part upon interconnecting the coupling components so that the fluid flow is diverted into the two different lumens of the flexible annular double lumen tube.

So when the flexible annular double lumen tube, the first coupling component, the second coupling component and the device are coupled together the gasket seals in a manner that establishes a continuous interior flow channel consisting of the first flow channel of the flexible annular double lumen tube, the first interior pipe of the male coupling part of the first coupling part, the second interior pipe of the second coupling part, and an interior flexible connection piece. A continuous exterior flow channel around the continuous interior flow channel is composed of the second flow channel of the flexible annular double lumen tube, the gap between the first interior pipe and first exterior pipe of the male coupling part of the first coupling part, the gap between the second interior pipe and the second exterior pipe of the second coupling component, and an annular gap between an exterior flexible connection piece and an interior flexible connection piece.

The gasket may have the shape of a basket that provides both an axial sealing length as well as radial sealing. A gasket bottom may conveniently have a central opening for passage of the second interior pipe of the first end fitting so that the first interior pipe and the second interior pipe can be put in direct fluid communication. The circumferential gasket may have a plurality of annularly, spaced apart, flow openings for establishing fluid communication between the gap between the second interior pipe and the second exterior pipe of the second coupling component and the gap between the first interior pipe and first exterior pipe of the male coupling part of the. Opposite the gasket bottom the opposite gasket end constitutes a sealing ring serving for axial sealing between the second exterior pipe and the first exterior pipe above the plurality of flow openings. The basket-shaped gasket is preferably made of rubber or similar known material for making gaskets.

The coupling system according to the present invention may further comprise a flow converter component adapted for converting a parallel flow from parallel tubes into an annular flow through the flexible annular double lumen tube via the second coupling component, wherein the converter component has a first converter end adapted to couple together with the first end fitting of the second coupling component. The second converter end of the flow converter component opposite the first converter end has parallel coupling ports adapted to dock into a valve or couple directly to parallel flexible tubes. The valve may e.g. be the valve described in the applicant's international application WO 2011/023196.

The first converter end advantageously merges internally into the second converter end via an orifice partition that serves to direct the annular flow channels into parallel flow channels. To that aspect the orifice partition may be configured with a first converter opening that provides fluid communication between the second interior pipe and one of the coupling ports, and a second converter opening that provides liquid communication between the annular flow gap between the second interior pipe and the second exterior pipe and the other coupling port.

The first converter end of the main converter body of the flow converter may have opposite third and fourth lock slots for slidingly, crosswise the longitudinal axis of the main converter body, receiving a second ring-shaped lock component adapted to, at least temporarily, lock the first end fitting of the second coupling component together with the first converter end of the flow converter. The second ring-shaped lock component has the same functionality as the ring-shaped lock component, and may also have a spring member.

BRIEF DESCRIPTION OF THE DRAWINGS

The invention will be described below by way of exemplary embodiments with reference to the drawing in which FIG. 1 is a perspective view of a cuffed irrigation catheter coupled to a flexible annular double lumen tube by means of the tube coupling system, FIG. 2 is a perspective view of a fragment of the flexible annular double lumen tube.

DETAILED DESCRIPTION OF SPECIFIC EMBODIMENTS

Figure 3:
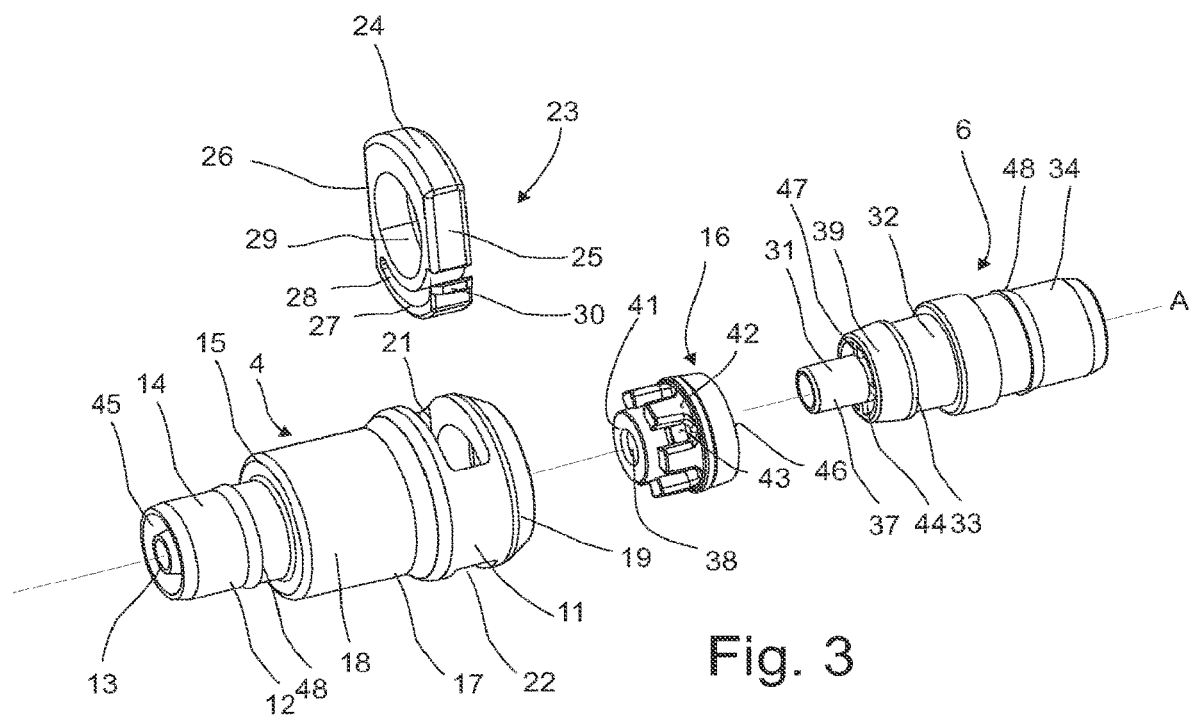
FIG. 3 is a perspective exploded view of the first coupling component and the second coupling component seen from the male coupling part of the first coupling component.

The invention is described below in relation to using a transanal catheter as an example of an irrigation catheter. It should be understood that the invention can be used in other context, such as e.g. irrigation via a stoma and that the individual components can be used separately, be dimensioned to fit flexible annular interior and exterior tubes having different diameters. The tubes are e.g. medical tubes, such as tubes having an internal diameter of 3-12 mm and a wall thickness of e.g. 1-2 mm.

FIG. 1 shows, in perspective, the main components of a tube coupling system 1 in inter-coupled state and coupled to a cuffed irrigation catheter 2.

The tube coupling system includes a flexible annular double lumen tube 3, a first coupling component 4 secured to a proximal end 5 of the flexible annular double lumen tube 3, a first second coupling component 6 secured to both the cuffed irrigation catheter 2 and the first coupling component 4, and a second coupling component 7 secured to a distal end 8 of the of the flexible annular double lumen tube 3 and to a flow converter component 9. The irrigation catheter 2 has a cuff 10 which in FIG. 1 is expanded.

The structure and configuration of the main components of the tube coupling system 1 and the cuffed irrigation catheter 2, are illustrated and described below with reference to sectional views and detailed figures.

Figure 4:
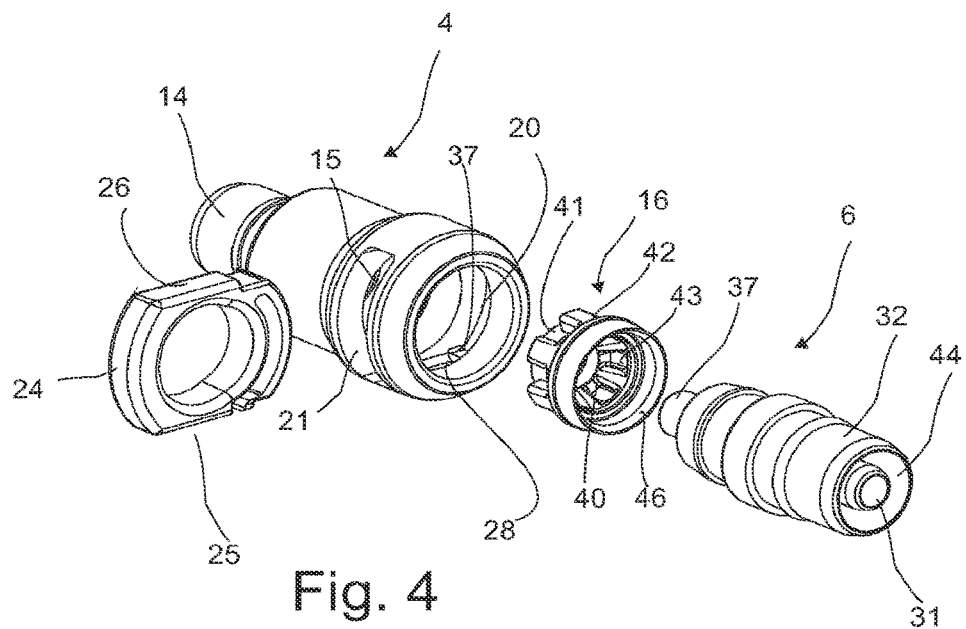
FIG. 4 shows the same seen from the second end fitting of the second coupling component.

As seen in the perspective views of FIGS. 3 and 4 the first coupling component 4 has a female coupling part 11 that axially extends into an opposite male coupling part 12. The male coupling part 12 has a first interior pipe 13 inside a first exterior pipe 14. The female coupling part 11 is wider than the male coupling part 12. The first interior pipe 13 extends along the longitudinal axis A of the male coupling part 12 and ends in a seat 15 at the bottom 16 of the female coupling part 11, which bottom 16 is provided at the internal transmission between the male coupling part 12 and the female coupling part 11. A gasket 16 is inserted into the female coupling part 11 against the seat 15. The exemplary gasket 16 is basket-shaped and will be described further below.

The female coupling part 11 has a first circumferential wall in axial extension of the exterior pipe 14 of the male coupling part 12. The first circumferential wall 17 delimits a first exterior pipe section 18 of increased exterior diameter in relation to the exterior diameter of the male coupling part 12. The first circumferential wall 17 extends axially into a second exterior pipe section 19 of increased exterior diameter in relation to the exterior diameter of the first exterior pipe section 18. The first exterior pipe section 18 has the seat 15, and the second exterior pipe section 19 provides the opening 20 of the first coupling component 4, and thus the passage for inserting the second coupling component 6.

The second exterior pipe section 19 has a first lock slot 21 opposite a second lock slot 22. A first ring-shaped lock component 23 is arranged slidingly through the lock slots 21,22 in order to lock the first coupling component 4 and the second coupling component 6 firmly together and to easily decoupled said coupling component 4,6.

The first ring-shaped lock component 23 has a first end 24 that, via opposite exterior straight slide surfaces 25,26, extends into an opposite second end 27. The second end 27 of the first ring-shaped lock component 23 has a spring member 28 that extends a sector of the circumference of the first ring-shaped lock component 23 to be radially flexible towards the center of the first ring-shaped lock component 23 to clamp around an inserted component, e.g. the second coupling component 4.

The first end 24 and the second end 27 of the first ring-shaped lock component 23 is curved substantially to follow the circumference of the second exterior pipe section 19, but other curvatures are within the scope of the present invention.

The length of the first lock slot 21 is selected to allow insertion of the first ring-shaped lock component 23 to allow the straight slide surfaces 25,26 to slide on slide means 28 on the interior perimeter of the second exterior pipe section 19. Such slide means could e.g. be slots, recesses, or shoulders, e.g. provided as or along opposite chords internally of the second exterior pipe section 19.

The curved first end 24 and the curved second end 27 curve away from each other, and the longest length between the first end 24 and the second end 27 is selected to allow at least the first end 24 to protrude from the first lock slot 21 to be used as a press button for application of radial force to lock the second coupling component 6 to the first coupling component 4, which second coupling component 6 is inserted via the central opening 29 of the first ring-shaped lock component 23. The second end 27 of the first ring-shaped lock component 23 is kept inside the second exterior pipe section 19 due to the annular extent of the annular spring member 28 being longer than the annular length of the second lock slot 22.

The free end 30 of the spring member 28 may be provided with first clamp means to clamp with second clamp means on any of the first ring-shaped lock component 23, the second exterior pipe section 19 or the second coupling component to ensure a firm coupling together of the first coupling component 4 and the second coupling component 6.

The first ring-shaped lock component 23 may also serve to provide an eccentric arrangement of the second coupling component 6 inserted in the female coupling part 11 via the opening 29 to move e.g. a shoulder of the second coupling component 6 below e.g. a breast 37 of the female coupling part 11. The second end 27 of the first ring-shaped lock component 23 is set free of any engagement and/or eccentric arrangement by pushing said second end 27 radially towards the first lock slot 21 via the second lock slot 22. So the first ring-shaped lock component 23 can be moved fully in and out of the second exterior pipe section 19 via the first lock slot 21 but not out of the second lock slot 22, which second lock slot 22 serves as a stop when a pressure force is applied to the first ring-shaped lock component 23 by pushing the first end 24.

The second coupling component 6 has a second interior pipe 31 that axially extends inside a second exterior pipe 32.

The second coupling component 6 has a first end fitting 33 adapted for coupling to the female coupling part 11 of the first coupling component 4, and it is the first end fitting 33 that is inserted via the opening 20 of the female coupling part 11 and the opening 29 of first ring-shaped lock component to temporarily lock the second coupling component 6 together with the female coupling component 4.

Opposite the first end fitting 33 the second coupling component 6 has a second end fitting 34 adapted for coupling to any of the flexible annular double lumen tube 3 or to similarly configured annularly arranged flexible connection pieces of an annular double lumen device 2 to establish fluid communication to a first flow channel 35 and a second flow channel 36 of the annular double lumen tube 3 via the interconnected first coupling component 4 and the second coupling component 6.

A first flow channel 35 and a second flow channel 36 are illustrated as being entirely concentric in FIG. 2, however because the interior flexible tube 3a is free to move radially inside the exterior flexible tube 3b concentricity is not always present and/or constant.

At the first end fitting 33 the second interior pipe 31 protrudes axially beyond the second exterior pipe 32 with a pipe extension 37 that fits to pass sealingly through a central opening 38 of the basket-shaped gasket 16, which is inserted in the female coupling part 11. Furthermore, at the first end fitting 33 the second exterior pipe 32 has a tapering 39 towards the pipe extension 37, which tapering 39 mates sealingly inside the compartment 40 of the basket-shaped gasket 16 when the second coupling component 6 is inserted lengthwise into said compartment 40 of the basket-shaped gasket 16, which is situated at the seat 15 of the first coupling component 4.

The gasket 16 has a gasket bottom 41 that extends into an circumferential gasket wall 42 provided with a plurality of annularly, spaced apart, flow openings 43 for establishing fluid communication between the gap 44 between the second interior pipe 31 and the second exterior pipe 32 of the second coupling component 6 and the gap 45 between the first interior pipe 13 and first exterior pipe 14 of the male coupling part 12 of the first coupling component 4.

A free gasket end 46 of the basket-shaped gasket 16 opposite the gasket bottom 41 constitutes a sealing ring between the second exterior pipe 32 and the first exterior pipe 14 above the plurality of flow openings 43.

The second interior pipe 31 and the second exterior pipe 32 are kept in annular spaced apart relationship by means of spacers 47 that extends radially between said second interior pipe 31 and said second exterior pipe 32. Such spacers may e.g. be ribs or struts.

The first interior pipe 13 and the first exterior pipe 14 are also kept in annular spaced apart relationship by means of spacers (not shown) that extends radially between said first interior pipe 13 and said first exterior pipe 14 in a manner similar as for the second interior pipe 31 and the second exterior pipe 32.

The second end fitting 34 and the male coupling part 12 both have an annular barb 48 in order to lock firmly to any of the annular double lumen tube 3 or to annularly arranged flexible connection pieces (not shown) of an annular double lumen device 2. The tapering 39 of the second exterior pipe 32 of the first end fitting 33 may serve the double function as also being a barb for some coupling applications. Also, the second interior pipe 31 may have barbs to improve frictional engagement to flexible tubes.

The first second coupling component 6 and the second coupling component 7 is an example of a coupling system for the flexible annular double lumen tube 3. The second coupling component 4 can be used at both the proximal end 5 and the distal end 8 of the flexible annular double lumen tube 3, and any of the end fittings 33,34 can be used for coupling to the flexible annular double lumen tube 3.

Figure 5:
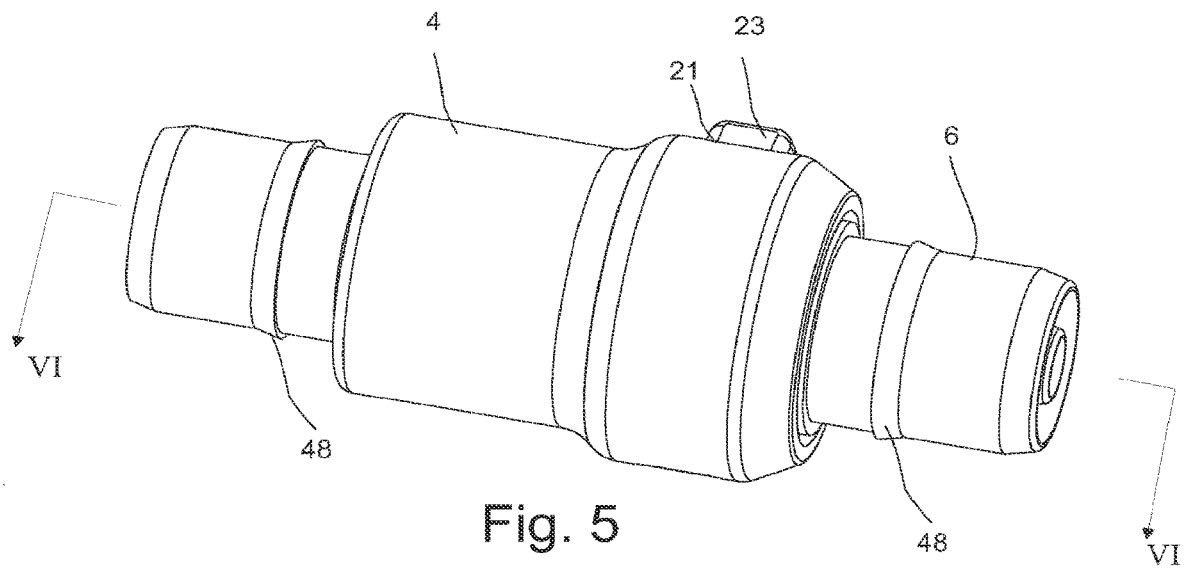
FIG. 5 shows, in perspective, the first coupling component locked together with the second coupling component.

In the perspective view of FIG. 5 the first coupling component 4 and the second coupling component 6 are assembled around the gasket 16, and the first ring-shaped lock component 23 locks these coupling components 4,6 together.

Figure 6:
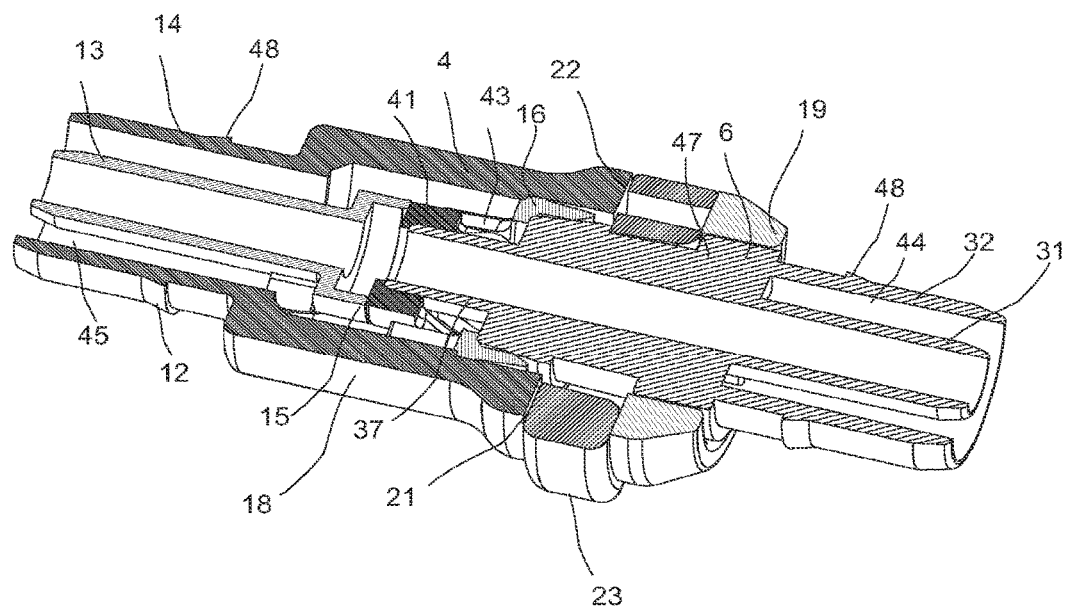
FIG. 6 is a lengthwise sectional view taken along line VI-VI in FIG. 5.

The lengthwise sectional view of FIG. 6 is taken through axial spacers 47. It should however be understood that below the spacers 47 a first length of a continuous interior flow channel 49 is provided and surrounded by a first length of a continuous exterior flow channel 50.

The first length of a continuous interior flow channel 49 is established by the lumen of the second interior pipe 31, the central opening 38 of gasket bottom 41 of the basket-shaped gasket 16, and the lumen of the first interior pipe 13.

The first length of the continuous exterior flow channel 50 is established by the gap 44 between the second interior pipe 31 and the second exterior pipe 32, which gap 44 is in fluid communication with the gap 45 between the first interior pipe 13 and first exterior pipe 14 of the male coupling part 12 of the first coupling component 4 via the plurality of annularly arranged flow openings 43 of the basket-shaped gasket 16.

Figure 7:
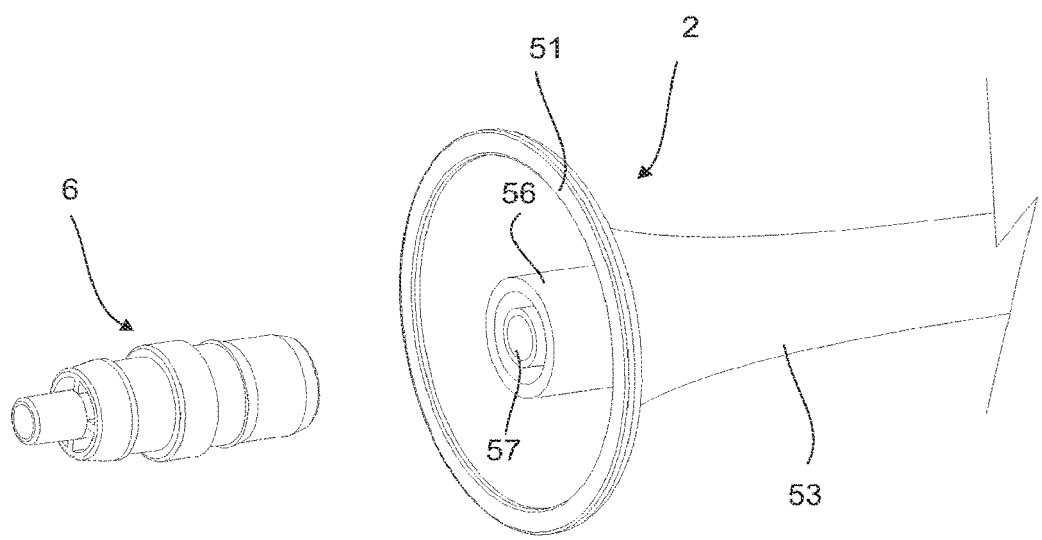
FIG. 7 is a fragmentary perspective view of a flared end of an irrigation catheter axially aligned with the second coupling component of the tube coupling system.

FIG. 7 is a fragmentary perspective view of a flared end 51 of the irrigation catheter 2, which is axially aligned with the second coupling component 6 of the tube coupling system of the present invention.

Figure 8:
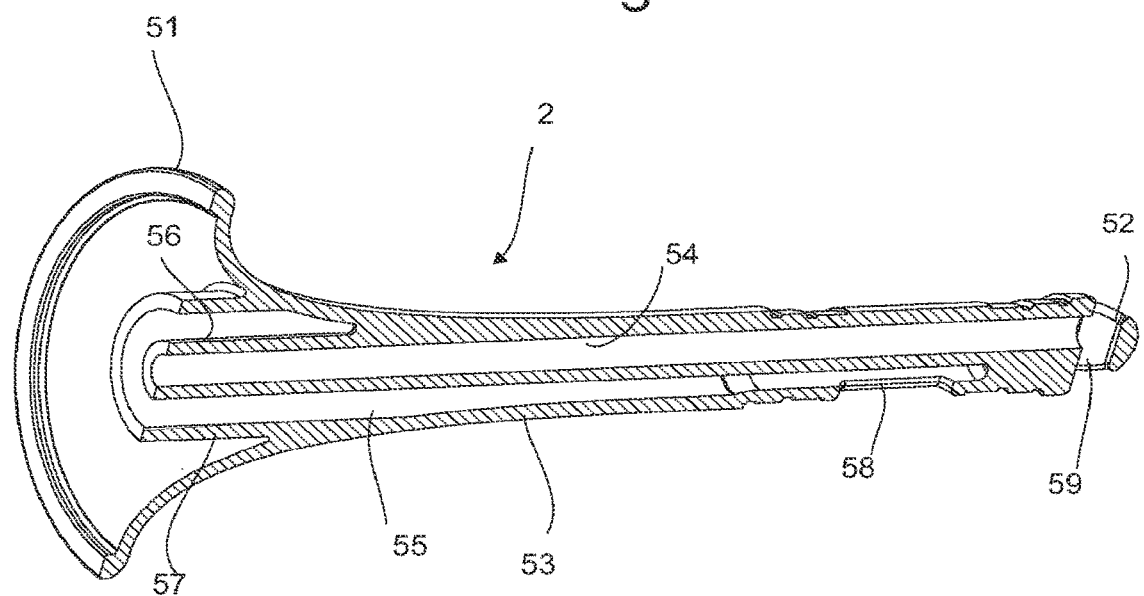
FIG. 8 is an axial sectional view of a modification of the irrigation catheter of the applicant's international patent application no. PCT/DK2017/050338, without the expandable cuff.

The irrigation catheter 2 can e.g. be the catheter described in the applicant's international patent application no. PCT/DK2017/050338, or the modification thereof seen in the axial sectional view of FIG. 8 and seen in fragment in FIG. 7.

The modified catheter 2 has annular arranged axially extending flow channels in form of axial flow conduits 54,55. The axial flow conduits 54,55 include an inner conduit 54 for delivering an irrigation liquid out through a free end 52 of the modified catheter 2 opposite the flared end 51 and an outer conduit 55 surrounding the inner conduit 54, which outer conduit 55 serves to deliver an expansion fluid to the expandable cuff (not shown in FIG. 8). The expansion fluid and the irrigation liquid may both be water or saline from the same reservoir (not shown) and the expanded cuff 10 be emptied into the body cavity into which the catheter part 53 opposite the flared end 51 is inserted and fixed by means of the expanded cuff. Suitable valve systems for this purpose may include but is not limited to the valve structures and valve principle described in the applicant's international patent applications no. PCT/DK2011/050021, PCT/DK2017/050338, and PCT/DK2010/050219.

The annularly arranged outer conduit 55 and the inner conduit 54 of the irrigation catheter 2 terminate at the flared end 51 into respective annularly arranged flexible outer connection piece 56 around inner connection piece 57, such as flexible tube pieces. Opposite the outer connection piece 56 the outer conduit 55 has an expansion fluid outlet 58 for inflating the cuff (not shown) and opposite the inner connection piece 57 the inner conduit 54 has one or more irrigation liquid outlets 59 for expelling irrigation liquid into the body cavity.

The annularly arranged flexible connection pieces 56,57 on the rigid irrigation catheter 2 can be made by 2K injection molding.

Figure 9:
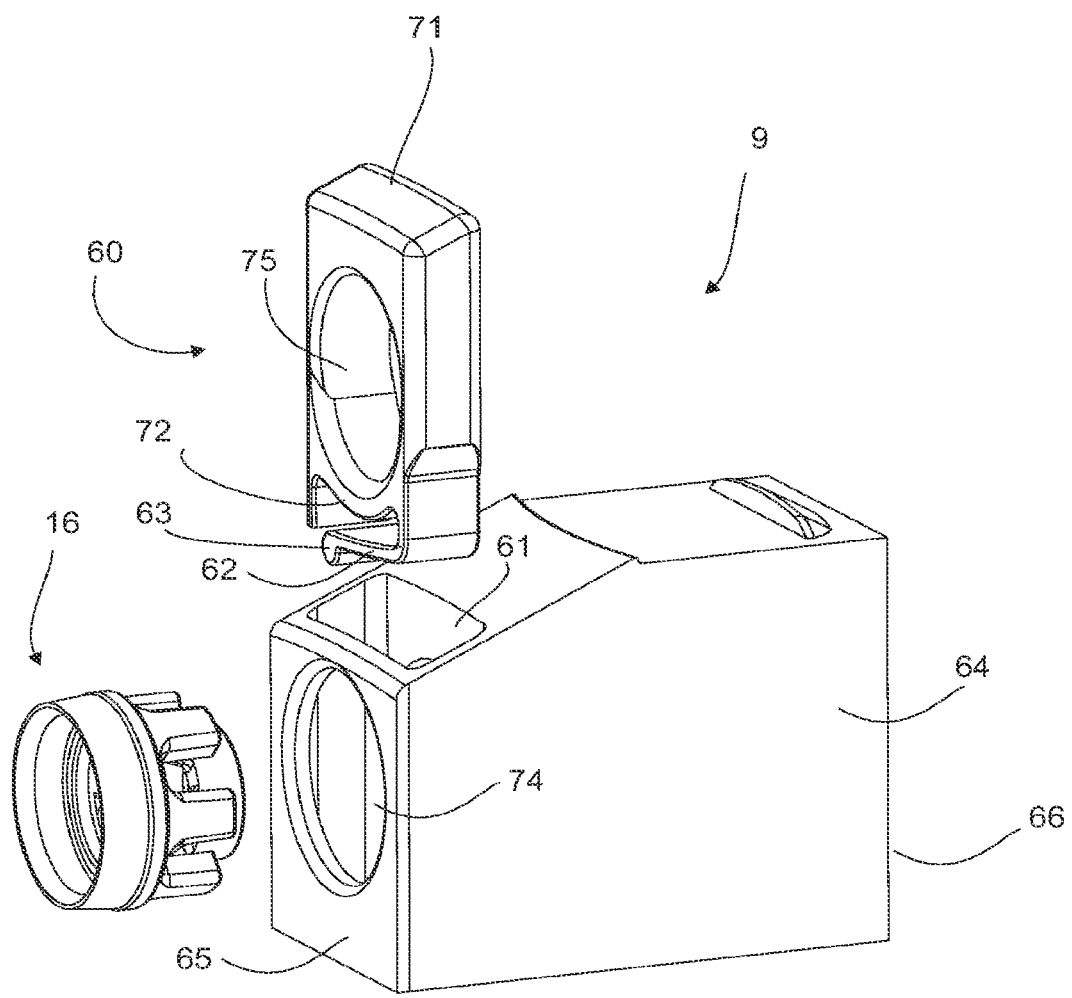
FIG. 9 is an exploded perspective view of a flow converter component seen from the first end for coupling to the flexible annular double lumen tube.

The tube coupling system for arranging the flexible annular double lumen tube in fluid communication with a reservoir of irrigation liquid and a reservoir of expansion fluid further includes a flow converter component 9, e.g. the flow converter component 9 seen in the perspective exploded view of FIG. 9.

As seen in FIG. 1 when a second second coupling component 7 is secured to the distal end 8 of the flexible annular double lumen tube 3 in a manner similar to the manner the first second coupling component 6 is secured to the proximal end of the flexible annular double lumen tube 3 an associated first end fitting 33 is exposed to connect to the flow converter component 9. The flow converter component 9 is adapted for converting a parallel flow from parallel tubes into an annular flow through the flexible annular double lumen tube 3 via the first end fitting 33 of the second second coupling component 7.

In order to lock the first end fitting 33 firmly together with the flow converter component 9, said flow converter component has a second ring-shaped lock component 60 and a basket-shaped gasket 16. The second ring-shaped lock component 60 has the same functionality and overall design as the first lock component 23, including being insertable via a lock slot, a third lock slot 61 that extends radial across the flow converter component 9. The second ring-shaped lock component also has an annular spring member 62 with a free end 63 provided with second clamp means (not shown) to clamp with second clamp means on any of the second ring-shaped lock component 61, or an interior coupling component of a main converter body in form of a flow converter housing 64.

Figure 10:
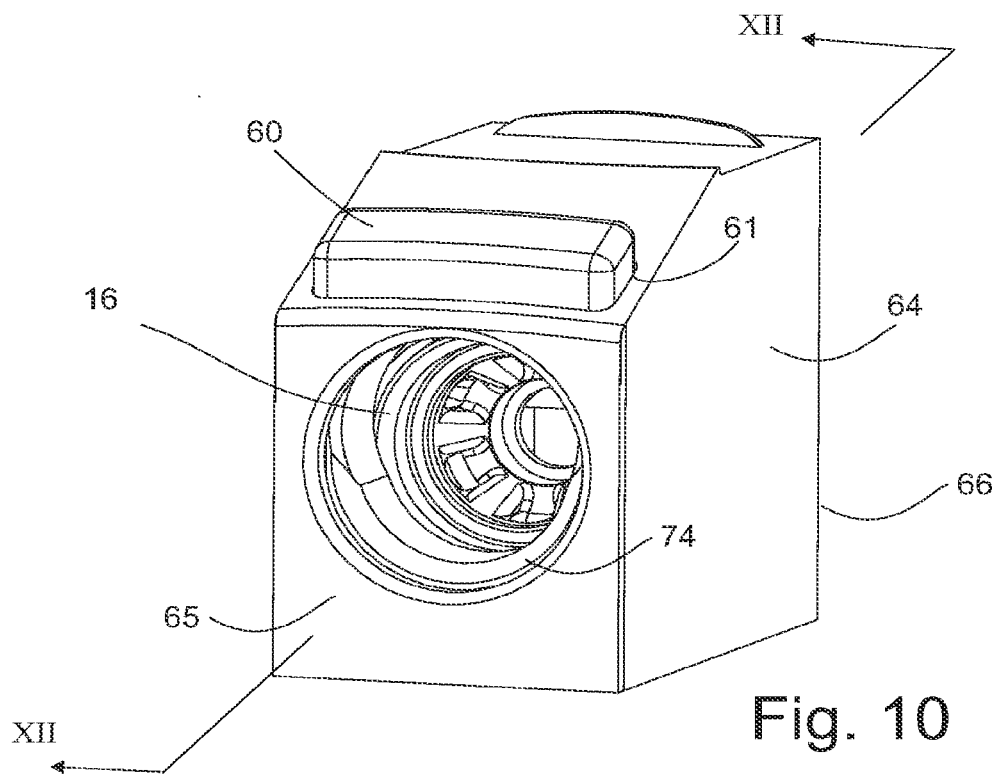
FIG. 10 shows the same in assembled state.
Figure 11:
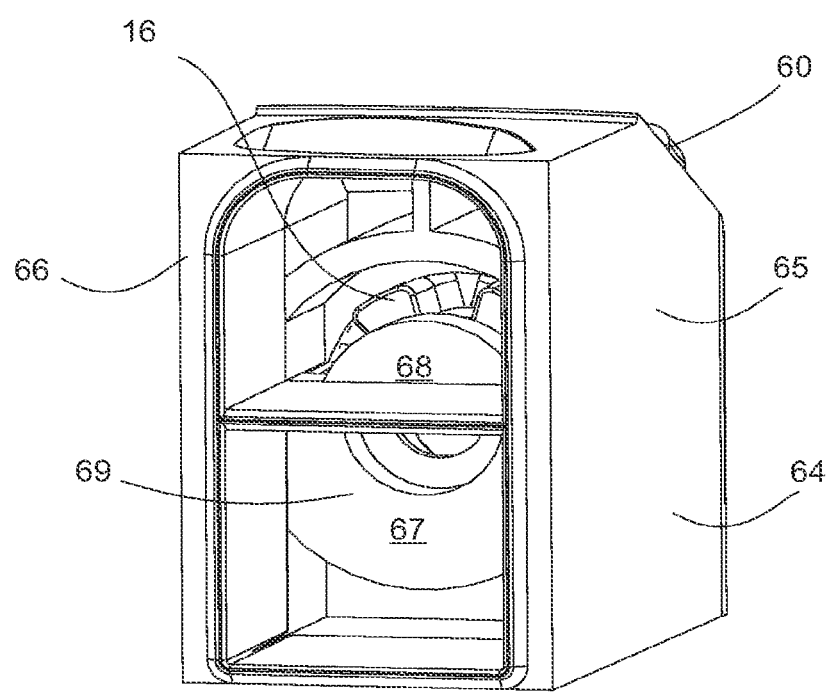
FIG. 11 shows the same from the second end opposite the first end.

As seen in FIGS. 9 and 10 the flow converter component 9 has a first converter end 65 adapted to couple together with the second end fitting 34 of the second coupling component 6, and, as seen in FIG. 11, a second converter end 66 opposite the first converter end 65 has parallel coupling ports 67,68 adapted to dock to a parallel terminals of a valve (not shown) or couple directly to parallel flexible tubes (not shown).

Figure 12:
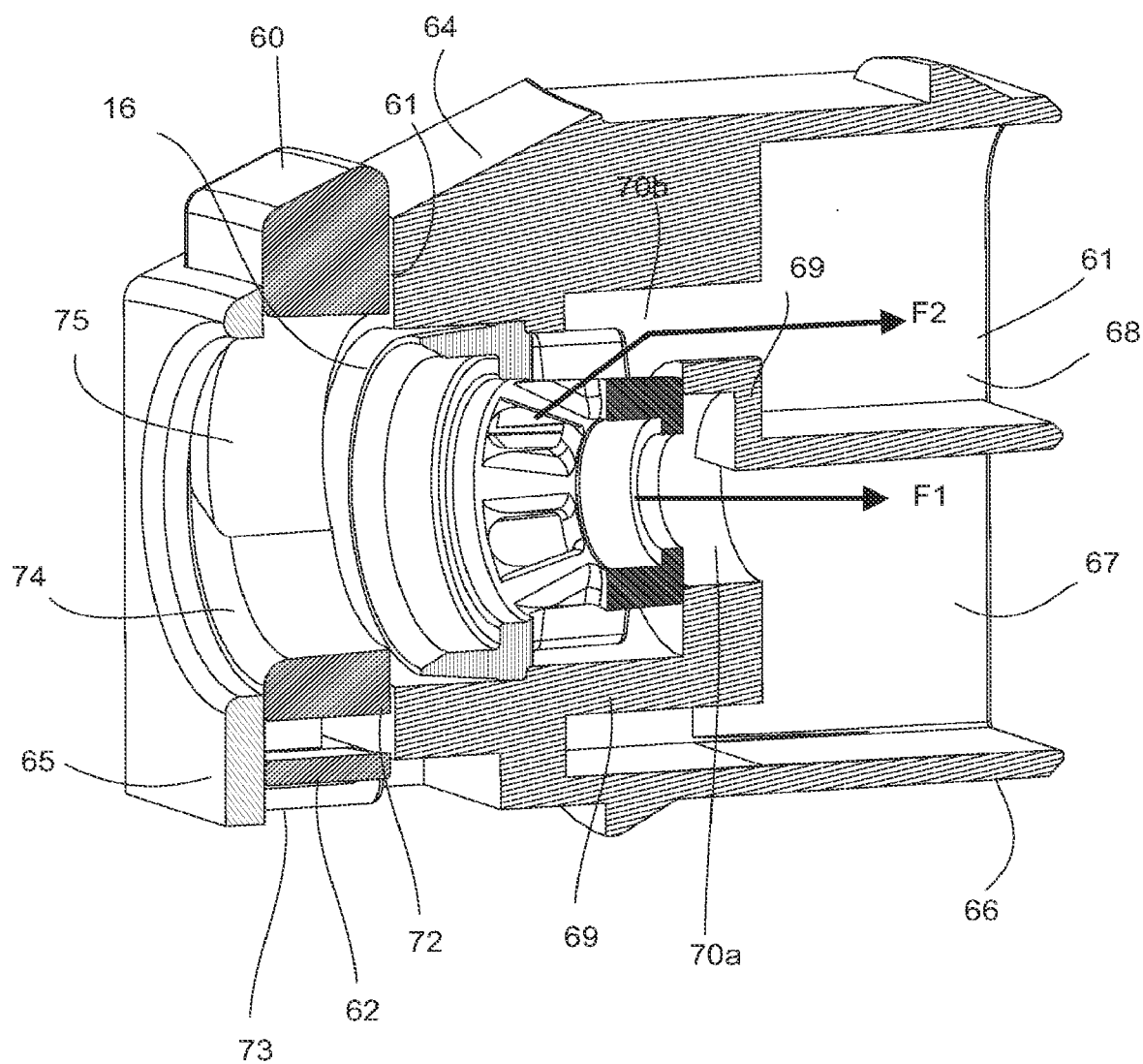
FIG. 12 is a sectional view taken along line XII-XII in FIG. 10.
Figure 13:
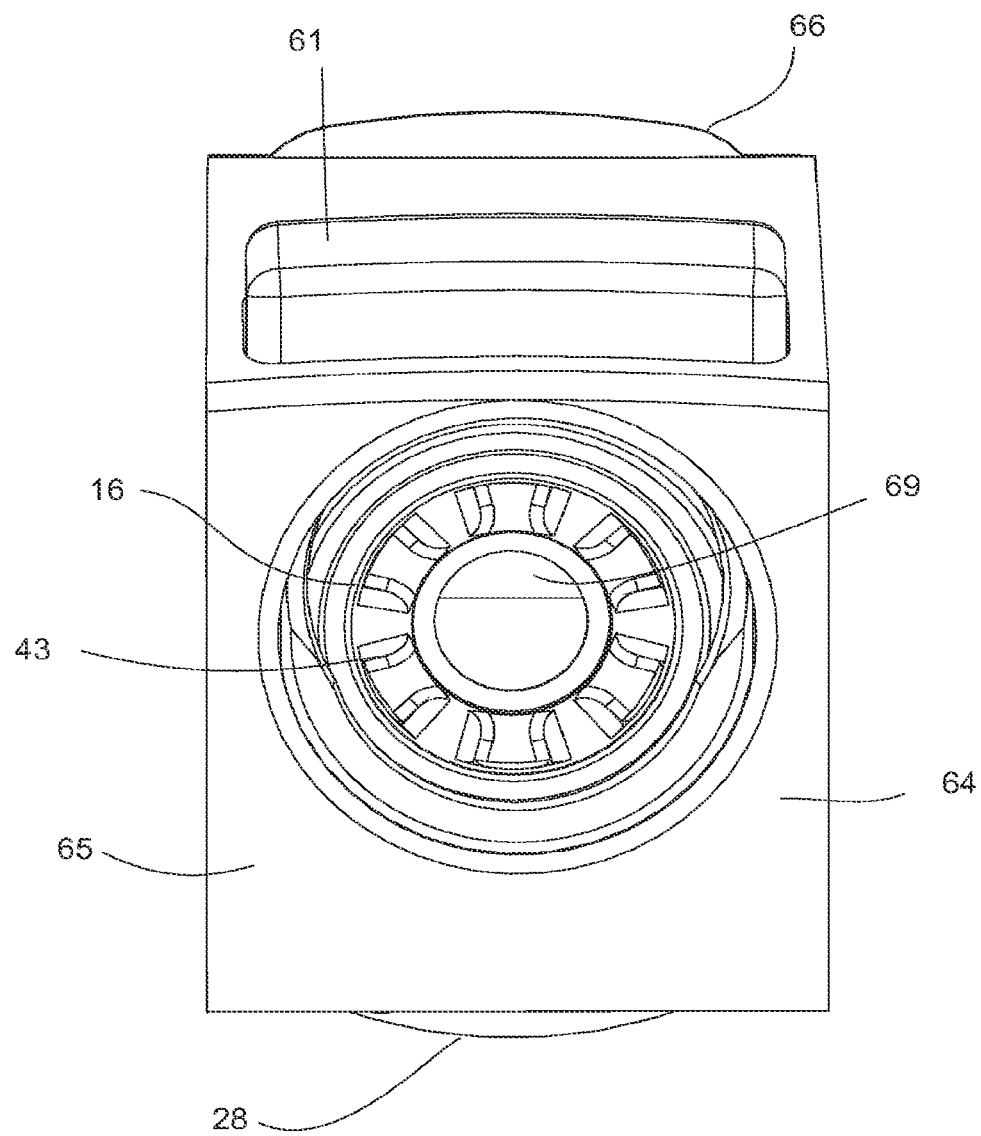
FIG. 13 is a front view of the flow converter component.

The first converter end 65 merges internally into the second converter end 66 via an orifice partition 69, which orifice partition 69 has a first converter opening 70a that can provide fluid communication between the second interior pipe 31 and one of a first coupling port 67, as indicated by arrow F1 in the axial sectional view of FIG. 12, and a second converter opening 70b that can provide fluid communication between the annular flow gap 44 between the second interior pipe 31 and the second exterior pipe 32 and a second coupling port 68 via the flow openings 43 of the basket-shaped gasket 16, as indicated by arrow F2 in the axial sectional view of FIG. 12, and as seen in the front view of FIG. 13.

The first converter end 65 of the housing 64 of the flow converter component 9 has the third lock slot 61 from which a first end 71 of the second ring-shaped lock component 60 protrudes to act as a pressure button to apply pressure to the spring member 62 at the opposite second end 72. The opposite second end 72 is accessible from outside housing 64 via a fourth lock slot 73 in order to release the locking engagement between the first end fitting 33 and the first converter end 65, when the first end fitting 33 is inserted via the central opening 73 of the second ring-shaped lock component 60 and the bore 74 of the first converter end 65.

The flexible annular double lumen tube and at least the first coupling component and the second coupling component can be implemented in many applications involving flow through tubes. The exterior and interior diameter of the coupling components are easily determined based on the diameter and the wall thickness of the exterior and interior diameters of the interior flexible tube and the exterior flexible tube, or vice versa by establishing the exterior and interior diameters of the interior flexible tube and the exterior flexible tube based on the exterior and interior diameter of the coupling components.

The invention claimed is:

1. A tube coupling system comprising a first tube coupling component comprising
   a male coupling part opposite a respective female coupling part, and
   a second tube coupling component comprising
   a first end fitting opposite a respective second end fitting,
   wherein the first tube coupling component has a first interior pipe that extends axially inside a first exterior pipe, the first interior pipe and the first exterior pipe being concentric,
   wherein the second tube coupling component has a second interior pipe that extends axially inside a second exterior pipe, the second interior pipe and the second exterior pipe being concentric,
   wherein the female coupling part of the first tube coupling component has a first exterior pipe section which has a seat for a gasket, which seat has its bottom at a transmission between the male coupling part and the female coupling part, which the gasket has a gasket bottom with a central opening for passage of the second interior pipe of the first end fitting, the gasket bottom extends into a circumferential gasket wall provided with a plurality of annularly, spaced apart, flow openings for establishing fluid communication between a gap between the second interior pipe and the second exterior pipe of the second tube coupling component, and between a gap between the first interior pipe and the first exterior pipe of the male coupling part of the first tube coupling component, and
   wherein a free gasket end of the gasket opposite the gasket bottom constitutes a sealing ring between the second exterior pipe and the first exterior pipe above the plurality of flow openings.

2. The tube coupling system according to claim 1, wherein the second interior pipe protrudes axially beyond the second exterior pipe with a pipe extension at the first end fitting of the second tube coupling component, but not at the second end fitting of said second tube coupling component.

3. The tube coupling system according to claim 1, wherein the first interior pipe and the second exterior pipe are kept in annular spaced apart relationship by means of spacers that extends radially between said second interior pipe and said second exterior pipe, optionally the spacers are ribs or struts.

4. The tube coupling system according to claim 1, wherein the second end fitting of the second tube coupling component and the male coupling part of the first tube coupling component have the same cross-section.

5. The tube coupling system according to claim 1, wherein the overall shape of the first tube coupling component has a funnel-shape, wherein the female coupling part is wider than the male coupling part, and in that the first exterior pipe has various diameters along its length.

6. The tube coupling system according to claim 1, wherein the female coupling part of the first tube coupling component has a first circumferential wall in axial extension of the first exterior pipe of the male coupling part, wherein the first circumferential wall delimits the first exterior pipe section of increased exterior diameter in relation to the exterior diameter of the male coupling part, the first circumferential wall extends axially into a second exterior pipe section of increased exterior diameter in relation to the exterior diameter of the first exterior pipe section.

7. The tube coupling system according to claim 1, wherein a circumferential wall of the first tube coupling component of the female coupling part has opposite first and second lock slots for slidingly, crosswise the longitudinal axis of the first tube coupling component, receiving a first ring-shaped lock component adapted to, at least temporarily, lock the first end fitting of the second coupling component together with the first tube coupling component.

8. The tube coupling system according to claim 7, wherein the first ring-shaped lock component has a first end that, via opposite exterior straight slide surfaces, extends into an opposite second end, optionally said first end curves away from said opposite second end, optionally following the exterior curvature of the female coupling part, and wherein a hole of the first ring-shaped lock component serves for inserting the first end fitting.

9. The tube coupling system according to claim 1, wherein the first tube coupling component is a single piece.

10. An irrigation system comprising the tube coupling system according to claim 8, a double lumen irrigation device, and an annular double lumen tube, wherein the tube coupling system inter-couples the double lumen irrigation device and the annular double lumen tube.

* * * * *